(12) United States Patent
Criscuolo et al.

(10) Patent No.: US 8,034,076 B2
(45) Date of Patent: Oct. 11, 2011

(54) ABSORBABLE FASTENER AND APPLYING APPARATUS

(75) Inventors: Christopher J. Criscuolo, Branford, CT (US); Russell S. Heinrich, Hamden, CT (US); Kourosh Azarbarzin, Fairfield, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 591 days.

(21) Appl. No.: 12/052,077

(22) Filed: Mar. 20, 2008

(65) Prior Publication Data

US 2008/0167668 A1   Jul. 10, 2008

Related U.S. Application Data

(63) Continuation of application No. 10/399,486, filed as application No. PCT/US01/50165 on Oct. 23, 2001, now abandoned.

(60) Provisional application No. 60/242,647, filed on Oct. 23, 2000.

(51) Int. Cl.
*A61B 17/08* (2006.01)

(52) U.S. Cl. .......... 606/219; 606/60; 606/232; 606/316; 606/317

(58) Field of Classification Search .......... None
See application file for complete search history.

(56) References Cited

U.S. PATENT DOCUMENTS

| | | | |
|---|---|---|---|
| 3,123,077 A | 3/1964 | Alcamo | |
| 4,402,445 A | 9/1983 | Green | |
| 4,454,875 A | 6/1984 | Pratt et al. | |
| 4,548,202 A | 10/1985 | Duncan | |
| 4,570,623 A | 2/1986 | Ellison et al. | |
| 4,723,540 A | 2/1988 | Gilmer, Jr. | |
| 4,805,617 A | 2/1989 | Bedi et al. | |
| 4,848,328 A | 7/1989 | Laboureau et al. | |
| 4,932,960 A | 6/1990 | Green et al. | |
| 5,002,562 A | 3/1991 | Oberlander | |
| 5,108,422 A | 4/1992 | Green et al. | |
| 5,169,400 A | 12/1992 | Mühling et al. | |
| 5,261,914 A | 11/1993 | Warren | |
| 5,354,292 A | 10/1994 | Braeuer et al. | |
| 5,454,814 A | 10/1995 | Comte | |

(Continued)

FOREIGN PATENT DOCUMENTS

EP    0 589 306 B1    3/1994

(Continued)

OTHER PUBLICATIONS

International Search Report from European Application No. EP 08 25 1988 mailed Oct. 17, 2008.

(Continued)

*Primary Examiner* — David H Willse
*Assistant Examiner* — Javier Blanco

(57) ABSTRACT

A surgical fastener apparatus, for securing a surgical mesh material to body tissue including a pair of anchors each having a retaining structure formed on an outer surface thereof; and a suture tether interconnecting the pair of anchors to one another. The pair of anchors have a substantially cylindrical body having a conically tapered distal end and a planar proximal end. The retaining structure includes a series of semi-circular angled projections having a planar proximal surface and a tapered distal end, wherein a center of each of the angled projections is spaced a distance from a longitudinal central axis of the body portion. The surgical fastener is made from a bioabsorbable material which reabsorbs into said body tissue at an appropriate rate, such as for example, polyglycolic acid and polylactic acid.

21 Claims, 8 Drawing Sheets

U.S. PATENT DOCUMENTS

| | | |
|---|---|---|
| 5,492,442 A | 2/1996 | Lasner |
| 5,500,000 A | 3/1996 | Feagin et al. |
| 5,593,423 A | 1/1997 | Person et al. |
| 5,662,655 A | 9/1997 | Laboureau |
| 5,728,116 A | 3/1998 | Rosenman |
| 5,730,744 A | 3/1998 | Justin et al. |
| 5,782,865 A | 7/1998 | Grotz |
| 5,891,146 A | 4/1999 | Simon et al. |
| 5,904,696 A | 5/1999 | Rosenman |
| 5,961,524 A | 10/1999 | Crombie |
| 5,964,768 A | 10/1999 | Huebner |
| 5,971,985 A | 10/1999 | Carchidi et al. |
| 5,993,476 A | 11/1999 | Groiso |
| 5,997,552 A | 12/1999 | Person et al. |
| 6,030,162 A | 2/2000 | Huebner |
| 6,036,701 A | 3/2000 | Rosenman |
| 6,045,573 A | 4/2000 | Wenstrom, Jr. et al. |
| 6,179,840 B1 | 1/2001 | Bowman |
| 6,187,009 B1 | 2/2001 | Herzog et al. |
| 6,190,401 B1 | 2/2001 | Green et al. |
| 6,290,701 B1 | 9/2001 | Enayati |
| 6,325,805 B1 | 12/2001 | Ogilvie et al. |
| 6,387,113 B1 | 5/2002 | Hawkins et al. |
| 6,540,751 B2 | 4/2003 | Enayati |
| 6,554,852 B1 | 4/2003 | Oberlander |
| 6,562,071 B2 | 5/2003 | Jarvinen |
| 2001/0004694 A1 | 6/2001 | Carchidi |
| 2001/0007074 A1 | 7/2001 | Strobel et al. |
| 2003/0032961 A1 | 2/2003 | Pelo et al. |
| 2003/0036755 A1 | 2/2003 | Ginn |
| 2003/0099102 A1 | 5/2003 | Duval |
| 2004/0254608 A1 | 12/2004 | Huitema et al. |
| 2006/0124688 A1 | 6/2006 | Racenet et al. |
| 2006/0273135 A1 | 12/2006 | Beetel |
| 2006/0291981 A1 | 12/2006 | Viola et al. |

FOREIGN PATENT DOCUMENTS

| | | |
|---|---|---|
| EP | 0 770 354 A1 | 5/1997 |
| EP | 1 025 803 A1 | 9/2000 |
| EP | 1293168 | 3/2003 |
| FR | 2 603 794 A1 | 3/1988 |
| FR | 2 642 641 A1 | 8/1990 |
| GB | 2269753 A | 2/1994 |
| JP | 09149906 | 6/1997 |
| SU | 1 034 734 A | 8/1983 |
| SU | 1 311 721 A | 5/1987 |
| WO | WO 01/062136 | 8/2001 |
| WO | WO 01/097677 | 12/2001 |
| WO | WO 02/30296 | 4/2002 |
| WO | WO 02/091932 | 11/2002 |
| WO | WO 03/034925 | 5/2003 |
| WO | WO 03/049906 | 6/2003 |

OTHER PUBLICATIONS

International Search Report from European Application No. EP 04 75 5078 mailed Jul. 2, 2008.

European Search Report for corresponding EP 10 008788, date of completion is Dec. 1, 2010 (3 pages).

ABSORBABLE FASTENER AND APPLYING APPARATUS

CROSS REFERENCE TO RELATED APPLICATION

The present application is a Continuation Application claiming the benefit of and priority to U.S. application Ser. No. 10/399,486, filed on Apr. 16, 2003 (now abandoned), which is a U.S. National Stage Application claiming the benefit of and priority under 35 U.S.C. 371, to International Application Ser. No. PCT/US01/50165, filed on Oct. 23, 2001, which claims the benefit of and priority to U.S. Provisional Application Ser. No. 60/242,647, filed Oct. 23, 2000, the entire contents of each of which is hereby incorporated by reference.

BACKGROUND

1. Technical Field

The present disclosure relates to a surgical fastener and to an apparatus for applying the surgical fastener as well as to a procedure for fastening objects to body tissue. More particularly, the present disclosure relates to an absorbable surgical fastener and apparatus for applying the absorbable fastener. In addition, the present disclosure relates to procedures for fastening an object to tissue and to procedures that require fastening of tissue together.

2. Background of Related Art

Fastening objects to body tissues is a commonly required task in many different surgical applications. One illustrative example of such an application is in hernia repair procedures wherein a reinforcing synthetic mesh material is attached to the tissue. A hernia is a general term referring to a protrusion of tissue through a wall of a cavity in which the tissue is normally contained, also called rupture. An inguinal hernia is a condition in which a loop of intestine enters the inguinal canal (i.e., a tubular passage through the lower layers of the abdominal wall). A direct inguinal hernia creates a bulge in the groin area, and an indirect hernia descends into the scrotum. In men, a hernia can develop at the point where the spermatic cord passes out of the abdomen into the scrotum. An inguinal hernia is a condition in males which occurs in approximately 2% of the male population. Often, an inguinal hernia can be pushed back into the abdominal cavity. However, if the inguinal hernia cannot be forced back through the abdominal wall, the herniated bowel may become trapped in the inguinal ring and/or strangulated. If the flow of blood is restricted (strangulated hernia) or the intestine is blocked (obstructed), emergency surgery is necessary. Without treatment, the strangulated loop of intestine dies as a result of a lack of blood to the loop of intestine.

In order to treat the inguinal hernia, surgery is often required to reposition the loop of intestine and secure the weakened muscles in the abdomen. There are two primarily practiced open surgical procedures for hernia repair which procedures use reinforcing synthetic mesh. One procedure is the Lichtenstein anterior repair method and the other is the Stoppa pre-peritoneal repair method. Modifications of these procedures exist, as do additional open surgical procedures that do not require the placement of reinforcing mesh over the hernia defect.

The Lichtenstein repair method is a "tension-free hemioplasty" based on two important facts, namely, inguinal hernias are caused by a metabolic disorder, which leads to a progressive destruction of the fibroconnective tissue of the groin, making the tissue unsuitable for use in hernia repair and the fact that traditional tissue repairs are associated with undue tension at the suture line, which leads to more postoperative pain, longer recovery time, and a higher rate of.

The Lichtenstein repair method includes the following steps. First, a transverse incision is made within a Langer's line, beginning from the pubic tubercle. The external oblique aponeurosis is opened and the spermatic cord with its cremasteric covering, external spermatic vessels, and the genital nerve are freed from the inguinal floor and lifted with a Penrose drain. The spermatic cord is then dissected free from the pubic bone area medial to the pubic tubercle in order to make room for extending the mesh beyond the pubic tubercle.

Next, the external oblique aponeurosis is dissected from the underlying internal oblique muscle and aponeurosis high enough to make room for a prosthesis. The sac is then dissected from the cord beyond its neck and inverted into the properitoneal space without ligation or excision. The proximal end is closed, dissected away from the cord structures, and inverted into the preperitoneal space. The medial side of the mesh is then shaped to the patient's anatomy. The first anchoring suture of the mesh fixes the mesh to the anterior rectus sheath where it inserts into the pubic bone. The lower edge of the mesh is sutured to the inguinal ligament using the same suture in a continuous fashion and ends at the lateral border of the internal ring. A slit is next made on the lateral end of the mesh, creating 2 tails. The upper tail is then passed under the cord and pulled toward the head of the patient, placing the spermatic cord in between the 2 tails. The upper tail is then crossed over the lower one and held with a pair of hemostats. The tails are later sutured together and tucked under the external oblique aponeurosis.

The Stoppa method of hernia repair places a single sheet of prosthetic material (i.e., surgical mesh) between the peritoneum and the musculopectineal orifice. The surgical mesh is then anchored to Cooper's ligaments using nonabsorbable sutures. The Stoppa hernia repair method is further described in the attached article in Appendix A, the entire contents of which are hereby incorporated by reference.

Yet another hernia repair method, known as TransAbdominal PrePeritoneal (TAPP) Laparoscopic Hernia repair method, generally includes the following steps. A pneumoperitoneum is created in the abdomen and an intra-abdominal pressure is maintained. The repair is then initiated. A laparoscope is then inserted and is pointed toward the afflicted inguinal canal. The peritoneal defect or hernia is identified. A peritoneal incision is made, which incision is extended from the lateral aspect of the inguinal region to the lateral umbilical ligament. The Cooper's ligament is then exposed as well as the inferior epigastric vessels and the spermatic Cord. The indirect inguinal hernia sac is then dissected carefully from the spermatic cord. A surgical mesh is then inserted into the intra-abdominal cavity and deployed over the inguinal region. There are three methods to place and secure the mesh over the inguinal region. The mesh is then secured in place with a surgical stapler. It is first stapled on to Cooper's ligament followed by placing several staples perpendicular to the ligament followed by a row more lateral and parallel to Cooper's Ligament. The graft is also anchored around the inferior epigastric vessels and lateral to them. If the mesh is wrapped around the spermatic cord, both limbs of the mesh are stapled closed. The peritoneum is then closed using additional staples and homeostasis is checked.

Yet another hernia repair method is known as Total Extra-Peritoneal (TEP) Laparoscopic Hernia repair method. This method is identical to the TAPP repair method, however, it entirely takes place in the preperitoneal space. The TEP method includes the following steps. Unlike the TAPP repair method, no pneumoperitoneum is created in the TEP repair method. Instead, a small incision is made below the umbilicus (midline) and the midline exposed. An incision is made slightly lateral to the midline aponevrosis and the anterior and posterior rectus muscle sheaths are exposed. The anatomy must first be clearly identified. Cooper's ligament should be first visualized as well as the inferior epigastric vessels. The indirect hernia sac should be bluntly pulled away from the spermatic cord and the inguinal canal. The hernia sac should then be dissected as medially as possible to allow a surgical mesh to cover the entire inguinal region. The mesh is then inserted and stapled into place as in the TAPP repair method. With the repair completed the small incisions can be closed.

The two most common of these methods are the Total ExtraPeritoneal (TEP) repair method and the TransAbdominal PrePeritoneal (TAPP) repair method. As discussed above, each of these methods utilizes a reinforcing synthetic mesh that must be fixed to the tissue to prevent early migration of the mesh away from the hernia site. However, the mesh must be anchored into place at first in order to prevent its movement from the hernia repair sight. Only after 7-10 days, does the mesh have sufficient tissue in-growth to prevent its motion away from the hernia repair site.

Each of the above disclosed procedures utilizes titanium staples to retain the mesh in place. These staples become permanent residents in the body cavity. A disadvantage of permanent metal staples is the possibility of the formation of excessive scar tissue (adhesions) which can in turn cause further patient complications and hinder future surgical procedures. In addition, these permanent staples may be associated with increased long-term discomfort to the patient as a result of the hernia repair procedure.

Accordingly, a need exists for an improved surgical fastener and applying apparatus as well as for methods in securing objects to body tissue, for example such as in attaching a mesh material for a sufficient time to a hernia repair site until sufficient tissue in-growth occurs to retain the mesh in place.

SUMMARY

It is an object of the present disclosure to provide an absorbable surgical fastener apparatus and methods in which the amount of foreign material in the patients body is reduced, thereby minimizing adhesion formation and reducing fastener-associated long-term discomfort to the patient.

It is another object of the present disclosure to provide an absorbable surgical fastener and method which is easier and faster to use than traditional suturing techniques in open procedures. Further, the relatively high firing force that can be applied to the absorbable fasteners of the present disclosure facilitate more reliable penetration of tougher tissue materials, such as for example, Cooper's ligament.

It is yet another object of the present disclosure to provide an absorbable surgical fastener which is radiolucent and provides greater peace of mind for the patient.

It is still a further object of the present disclosure to provide an absorbable surgical fastener apparatus having a suture tether disposed between anchoring barbs. The tether provides the advantage of holding the mesh in place loosely thus minimizing the tension in the surrounding tissue and reducing fastener pull-out occurrences.

It is another object of the present disclosure to provide a surgical fastener apparatus which is dimensioned to not penetrate the abdominal wall of the patient and which is provided with a series of barbs having a relatively larger surface than standard fastener barbs to thereby better retain the fastener in soft tissue.

The presently disclosed surgical fastener apparatus and method serve the function of previously used staples to secure objects to body tissue as performed in previous methods, for example, mesh being fixed to specific anatomic landmarks surrounding the hernia repair, or attaching mesh to tissue, or attaching tissue to tissue or attaching tissue to ligaments. However, the presently disclosed absorbable fastener apparatus and method have the uniquely advantageous feature that the absorbable fasteners are utilized to attach the mesh to the tissue for a sufficient time to allow tissue in-growth to occur on the mesh material. In this manner, the absorbable fasteners help prevent early mesh migration and then after sufficient tissue in-growth are absorbed in the body.

A surgical fastener apparatus is provided for securing a surgical mesh material to body tissue, in which the apparatus includes a pair of anchors each having retaining means formed on an outer surface thereof and a suture tether interconnecting said pair of anchors to one another. The fastener apparatus is preferably made from a bioabsorbable material and is dimensioned such that the apparatus will only be partially absorbed over a period of 2 to 3 weeks after implantation and will be completely absorbed into the body at any time thereafter.

In an alternate embodiment, the surgical fastener apparatus includes a conical body portion having a pointed distal tip and an enlarged proximal head. The conical body portion being provided with a helical thread commencing at or near the distal tip and terminating preferably at a distance spaced from the enlarged proximal head.

In addition, a hernial repair method utilizing the fasteners in accordance with the present disclosure is provided in which a surgical mesh is secured in place over the hernia repair site by imbedding the surgical fasteners in to body tissue through the surgical mesh.

BRIEF DESCRIPTION OF THE DRAWINGS

Various embodiments of the presently disclosed surgical fastener and methods will be described herein with reference to the accompanying drawing figures wherein.

DETAILED DESCRIPTION OF PREFERRED EMBODIMENTS

Figures 1, 2:
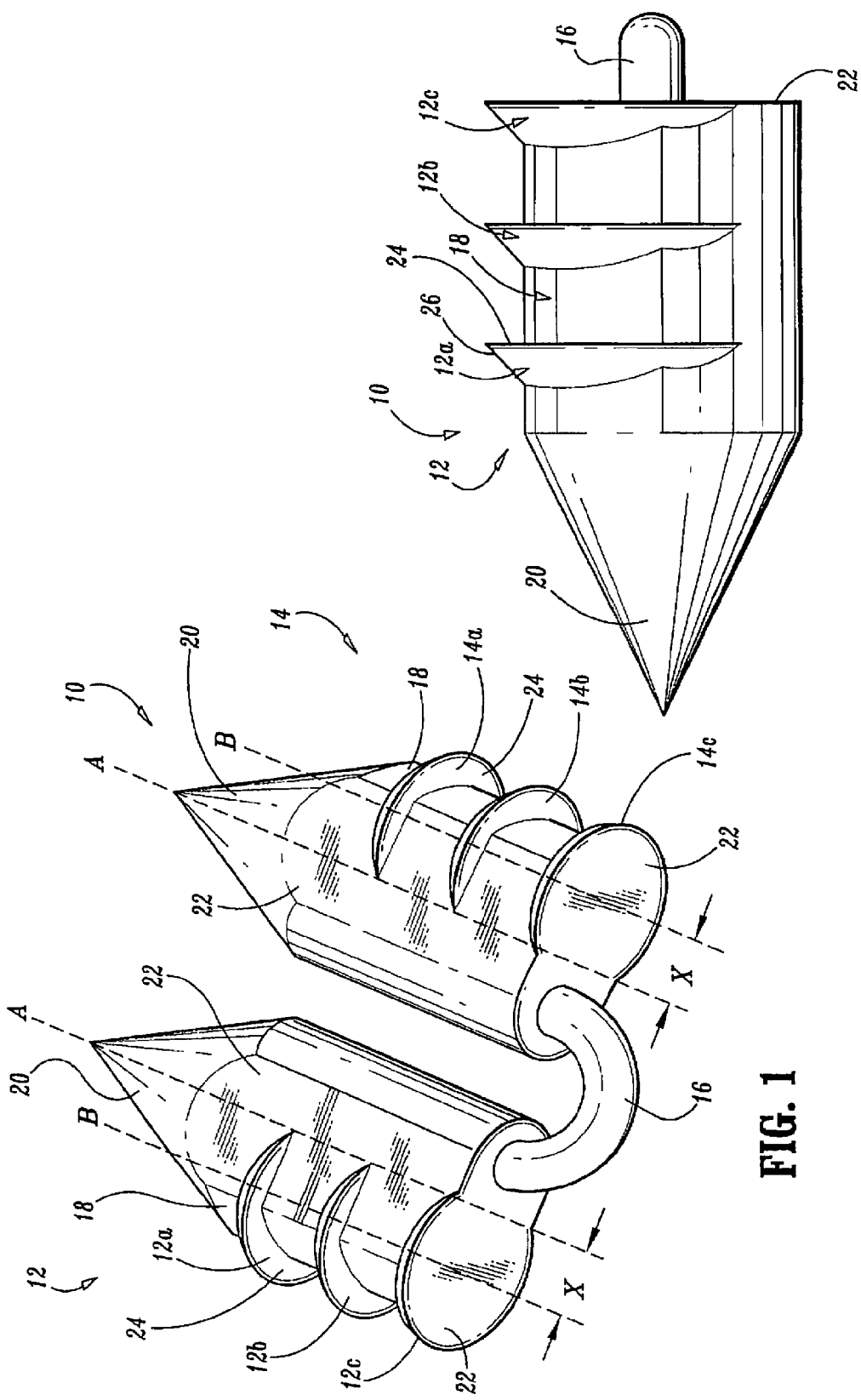
FIG. 1 is an enlarged perspective view of one embodiment of an absorbable surgical fastener apparatus constructed in accordance with the present disclosure.
FIG. 2 is a side view of a barb portion of the absorbable surgical fastener apparatus of FIG. 1.

Preferred embodiments of the presently disclosed absorbable surgical fastener apparatus and method of applying same will now be described in detail with reference to the drawing figures wherein like reference numerals identify similar or identical structural elements.

The presently disclosed absorbable surgical fastener apparatus and method is shown and described herein in connection with open and laparoscopic inguinal, femoral and ventral hernia repairs. Although not described in detail herein, the absorbable fastener can also be applied to other procedures which require that objects be attached to body tissue.

Referring initially to FIGS. 1 and 2, an absorbable surgical fastener apparatus for connecting objects to body tissue, such as absorbable fastener 10 includes dual fastener anchors 12 and 14 secured to one another by a suture tether 16 extending therebetween. Each anchor 12 and 14 has a substantially cylindrical body portion 18 having a conically tapered distal end 20 and a substantially planar proximal end surface 22. Anchors 12 and 14 are preferably provided with conically shaped distal ends 20 for easier penetration of anchors 12 and 14 into hard tissues, such as, for example, Cooper's ligament. While a generally conical distal end has been disclosed, it is envisioned that other shaped ends (e.g., pyramid, and the like) can be provided. Each anchor 12 and 14 is provided with a pair of opposed flattened side surfaces 22 extending longitudinally along the length thereof.

Anchors 12 and 14 are provided with barbs 12a, 12b, 12c, and 14a, 14b, 14c respectively to inhibit fastener pull-out occurrences in either hard or soft tissue. Each barb is semicircular having a planar proximal surface 24 which is orthogonal to a central longitudinal axis "A" of each anchor 12 and 14, and a tapered lower surface 26. Preferably, barbs 12a-12c and 14a-14c share a common central axis "B", however, it is envisioned that each respective barb can have a different center as compared to other barbs on the anchor. Preferably, central axis "B" is spaced a distance "X" from longitudinal axis "A". In this manner, the center of barbs 12a-12c and 14a-14c can be positioned to reveal a greater amount of planar proximal surface 24 in order to provide an anchor with predetermined anchoring and securing characteristics for body tissue without compromising the strength of body portion 18 of each anchor 12 and 14. For example, if greater retaining strength is desired, distance "X" between central axis "B" and longitudinal axis "A" is increased thereby forming a bard with a larger planar proximal surface 24. In the case of securing a fastener to soft tissue, as is the case in hernia repair, a fastener having a larger projecting barb is desired in order to better anchor the fastener into the soft tissue of the patient.

Figure 2A:
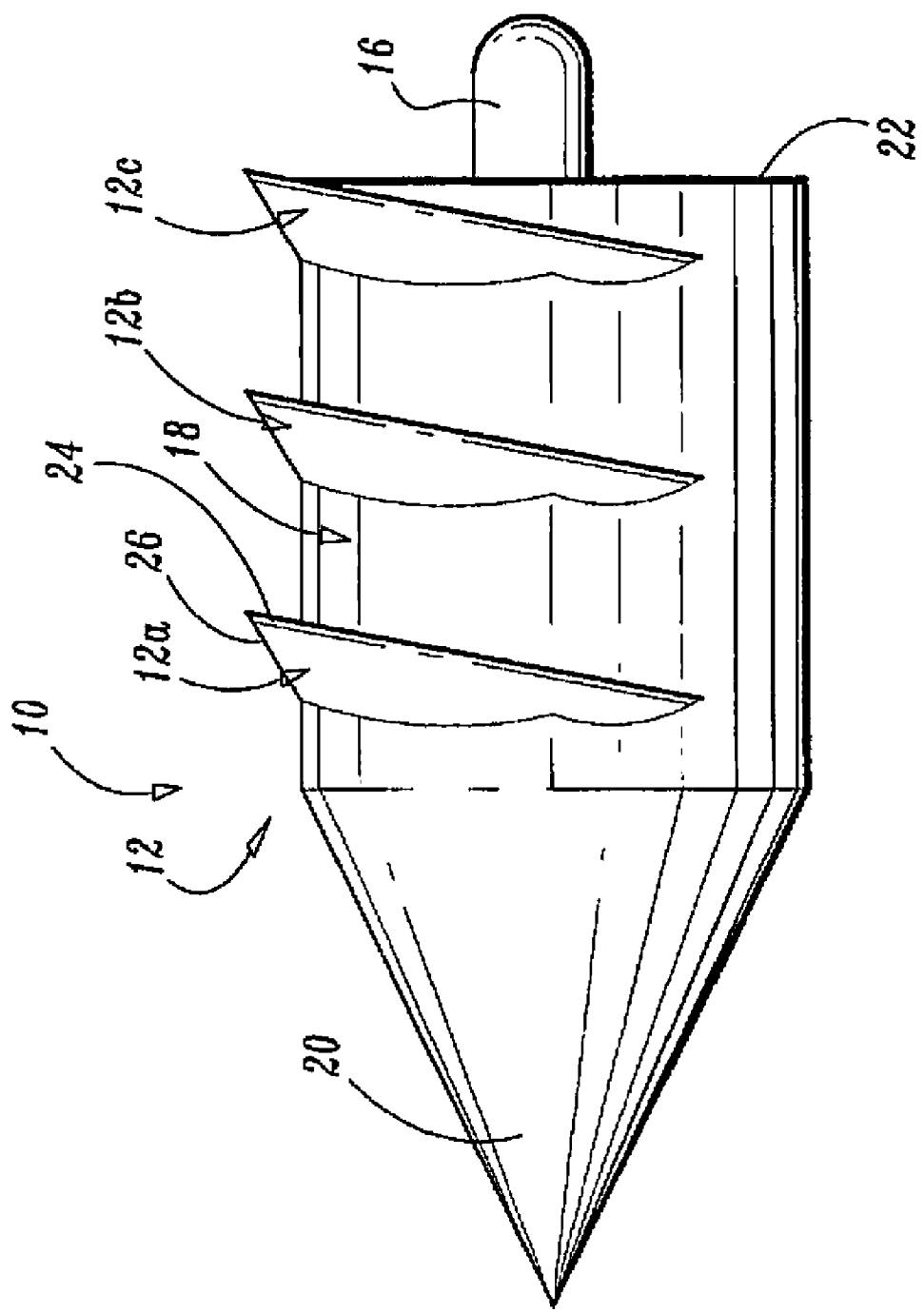
FIG. 2A is a side view of a barb portion of an absorbable surgical fastener apparatus according to an alternate embodiment of the present disclosure.

While each barb 12a-12c and 14a-14c is orthogonal to longitudinal axis "A" of each anchor 12 and 14 respectively, as seen in FIG. 2A, it is envisioned that each barb can be angled relative to longitudinal axis "A" such that barbs 12a, 12b and 12c form a partial thread around body portion 18 of each anchor 12 and 14. In this manner, as each anchor 12 and 14 is pressed into body tissue, each anchor 12 and 14 will rotate into the body tissue.

Although the embodiment of FIGS. 1 and 2 illustrate barbs formed partially around the circumference of anchors 12 and 14, multiple barb configurations can be utilized and are within the scope of the present disclosure. For example, in addition to the illustrated configuration, single barb, circumferential barb (i.e., barbs encircling the entire anchor), sharp barbs, dull barbs, multiple barbs, and various geometrically shaped barbs may be utilized.

While a planar proximal end 20 has been shown, it is envisioned that each anchor 12 and 14 can be provided with a notch or detent (not shown) formed in the proximal end thereof. In this manner, when a series of absorbable fasteners 10 are joined together, the tapered distal ends 18 are received in the detents to thereby maintain the absorbable fasteners 10 and anchors 12 and 14 longitudinally aligned with one another.

Absorbable fasteners 10 are preferably made of medical grade absorbable materials, for example, Polyglycolic Acid (PGA) and Polylactic Acid (PLA). A critical feature of the presently disclosed absorbable fastener is that the absorbable fastener provide sufficient strength to retain a mesh material in place for a desired period of time. For example, in the case of applying a hernia repair mesh material, it is recommended that absorbable fasteners 10 remain in place retaining the mesh material for approximately 2-3 weeks and be absorbed into the body tissue anytime after that.

It is preferred that absorbable fasteners 10 are approximately 3 mm long, from the tip of distal end 18 to proximal end 20, by approximately 1.5 mm in diameter. Other suitably configured and dimensioned fasteners may also be utilized depending on the particular application. It is also preferred that absorbable fasteners 10 are configured and dimensioned to avoid penetrating too far into the tissue. An example of a similar fastener structure and an instrument for applying such fasteners are disclosed in U.S. Pat. No. 5,997,552 (hereinafter "the '552 patent"), issued to Person et al. and entitled Meniscle Fastener Applying Device, the entire contents of which are hereby incorporated by reference. Unlike the fastener in the '552 patent, the barbs of fastener 10 according to the present disclosure have a center "B" which is spaced a distance "X" from the longitudinal axis "A" of the anchor as opposed to the body of the anchor being cut away to reveal a barb in the '552 patent. In this manner, a barb having a larger height is achieved without altering the dimensions of the body portion, which larger height more firmly secures the anchor of fastener 10 into body tissue as compared to the fastener disclosed in the '552 patent.

Unlike the applicator instrument for placing absorbable fasteners 10 disclosed in U.S. Pat. No. 5,997,552, previously incorporated by reference herein, the applicator according to the present disclosure is preferably adapted to fire 20 to 30 fasteners per instrument for use in either open and/or laparoscopic procedures. It is envisioned that the applicator instrument be either entirely disposable after use or be provided with a replaceable cartridge of fasteners which can be coupled to the end of a reusable applicator and replaced within a given procedure while the handle of such an applicator would still be disposable but would be reusable within a single procedure. While an alternate applier may be used, the fastener applier disclosed in the '552 reference can be used to apply the surgical fasteners disclosed herein.

By way of example, the general procedure of applying a mesh material during a hernia repair procedure, is to first create an access to the location of the hernia (i.e., incision and dissection) thereby exposing the hernia; then place a prosthetic mesh over the hernia defect; next fasten the mesh to the surrounding tissue by firing a plurality of absorbable fasteners 10 through the mesh and into tissue to thereby secure the mesh into place; and finally close the access wound.

Figure 3:
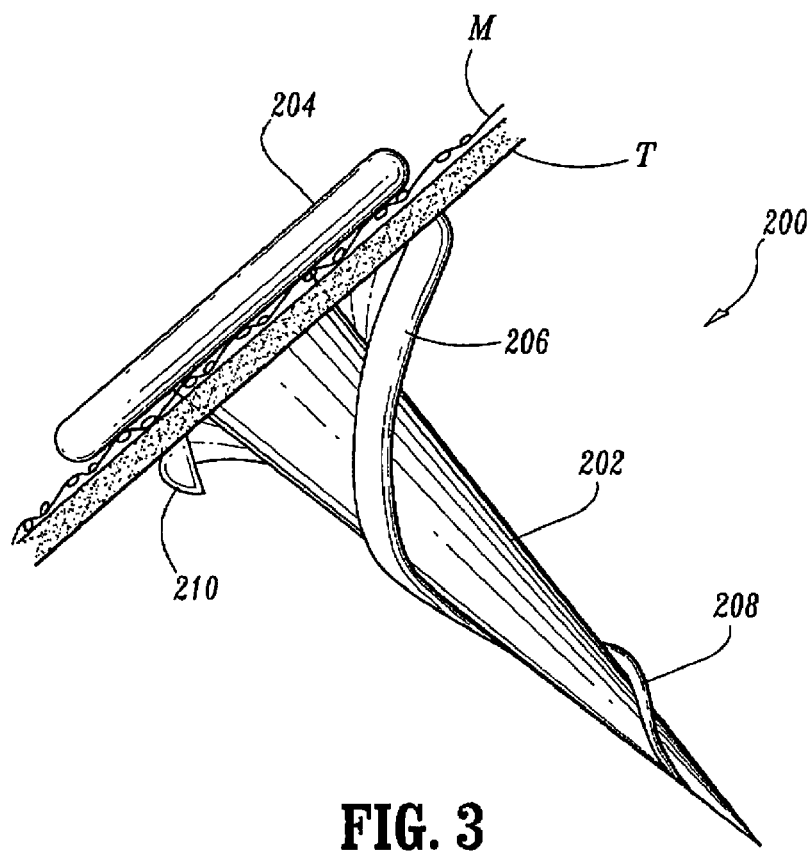
FIG. 3 is an enlarged perspective view of an alternative embodiment of an absorbable surgical fastener in accordance with the present disclosure.
Figure 4:
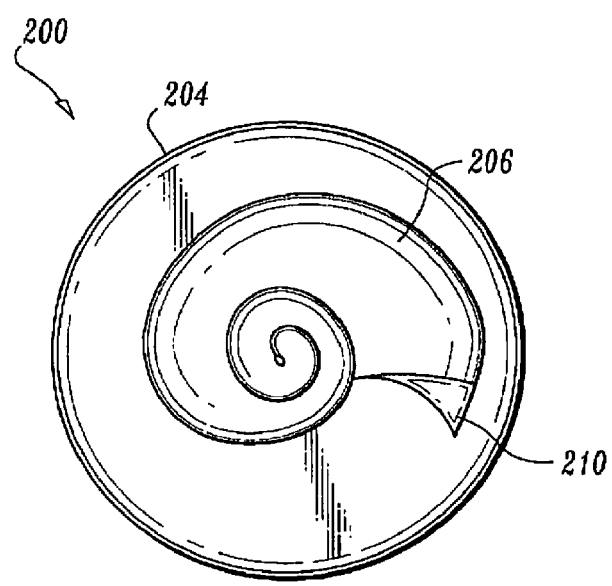
FIG. 4 is an end view of the surgical fastener of FIG. 3.
Figure 5:
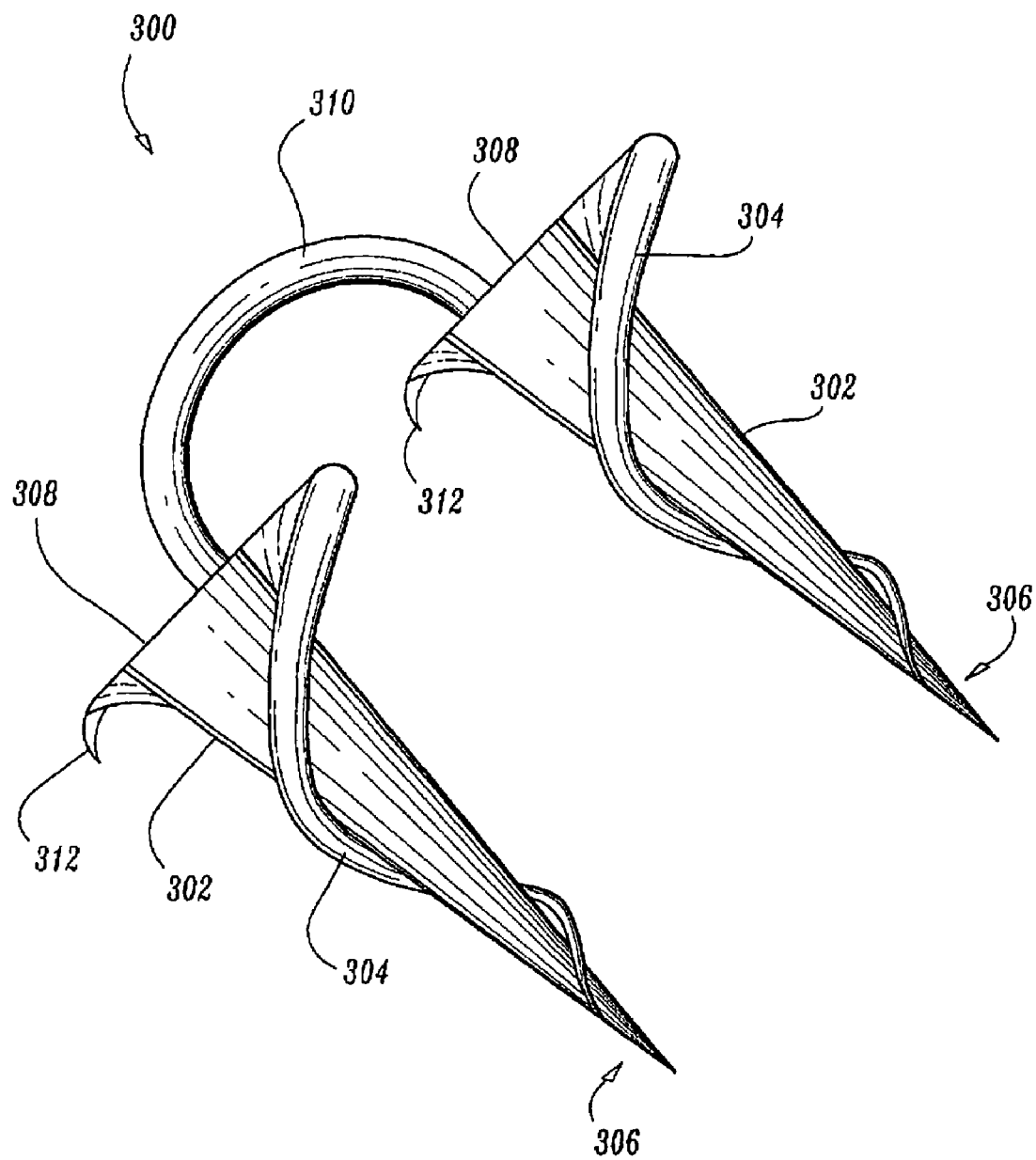
FIG. 5 is an enlarged perspective view of an absorbable surgical fastener apparatus including a pair of fasteners as shown in FIG. 3.

Turning now to FIGS. 3-5, an alternative embodiment of a surgical fastener in accordance with the present disclosure in shown generally as 200. As seen in FIGS. 3 and 4, fastener 200 includes a substantially conical body portion 202 depending from a circular head portion 204. Conical body portion 202 includes a helical thread 206 commencing at a pointed distal tip 208 of body portion 202 and terminating at a distance spaced from head portion 204. As the helical thread 206 advances from distal tip 206 toward head portion 204, the radial projection of the helical thread 206 from the body portion 202 increases. While the helical thread 206 is disclosed as commencing at the distal tip 208, it is envisioned that the helical thread 206 can commence at a distance spaced from the distal tip 208. In addition, head portion 204 can be provided with a recess or notch (not shown) formed in the center of the proximal surface thereof. The recess being configured to receive the distal tip 208 of an adjacent fastener 200 therein. In this manner, a series of fasteners 200 can be aligned in a tip-to-tail fashion with one another and share a common axis.

In use, fastener 200 is pressed into body tissue "T", through surgical mesh "M", until the entire body portion 202 of fastener 200 has passed through mesh "M" and has been buried in tissue "T". Head portion 204 ensures that fastener 200 does not completely pass through mesh "M" thereby ensuring that mesh "M" is in contact with tissue "T". Fastener 200 includes an arcuate tooth 210 projecting radially outwardly from the proximal end of helical thread 206 and oriented such that the curve of the arcuate tooth 210 is oriented to inhibit a rotation of fastener 200 which would remove fastener 200 from body tissue "T".

Turning now to FIG. 5, a surgical fastener apparatus according to the present disclosure is shown generally as 300. Similar to fastener 200, surgical fastener apparatus 300 includes a pair of substantially conical anchors 302 each having a helical thread 304 commencing at a distal tip 306 of each anchor 302 and terminating at a proximal end surface 308 of each anchor 302. Once again, the radial projection of the helical thread 304 on anchor 302 increases as the helical thread 304 advances from the distal tip 306 to the proximal end of the anchor 302. While the helical thread 304 is disclosed as commencing the distal tip 306, it is envisioned that the helical thread 304 can commence at a distance spaced from the distal tip 306 just as well. Anchors 302 are connected to one another by a suture tether 310 extending therebetween. As seen in FIG. 5, the orientation of helical thread 304 on each anchor 302 is in the same direction. In this manner, as anchors 302 are being imbedded into body tissue and commence rotating in the direction of helical thread 304, suture tether 310 on each anchor 302 will rotate in the same direction and not become tightened. The proximal end of each helical thread is provided with an arcuate tooth 312, which arcuate tooth 312 is oriented such that after anchors 302 have been completely imbedded into the body tissue the tooth 312 will dig into the body tissue if the anchor is rotated in a direction which would remove the anchor from the body tissue. Similar to fastener 10, surgical fastener apparatus 300 can be provided with a detent or recess 314 (see FIG. 6) formed in the proximal end surface thereof. In this manner, a series of fasteners 300 can be aligned in tip-to-tail fashion with one another in a fastener applier so that fasteners 300 share a common axis.

Figure 6:
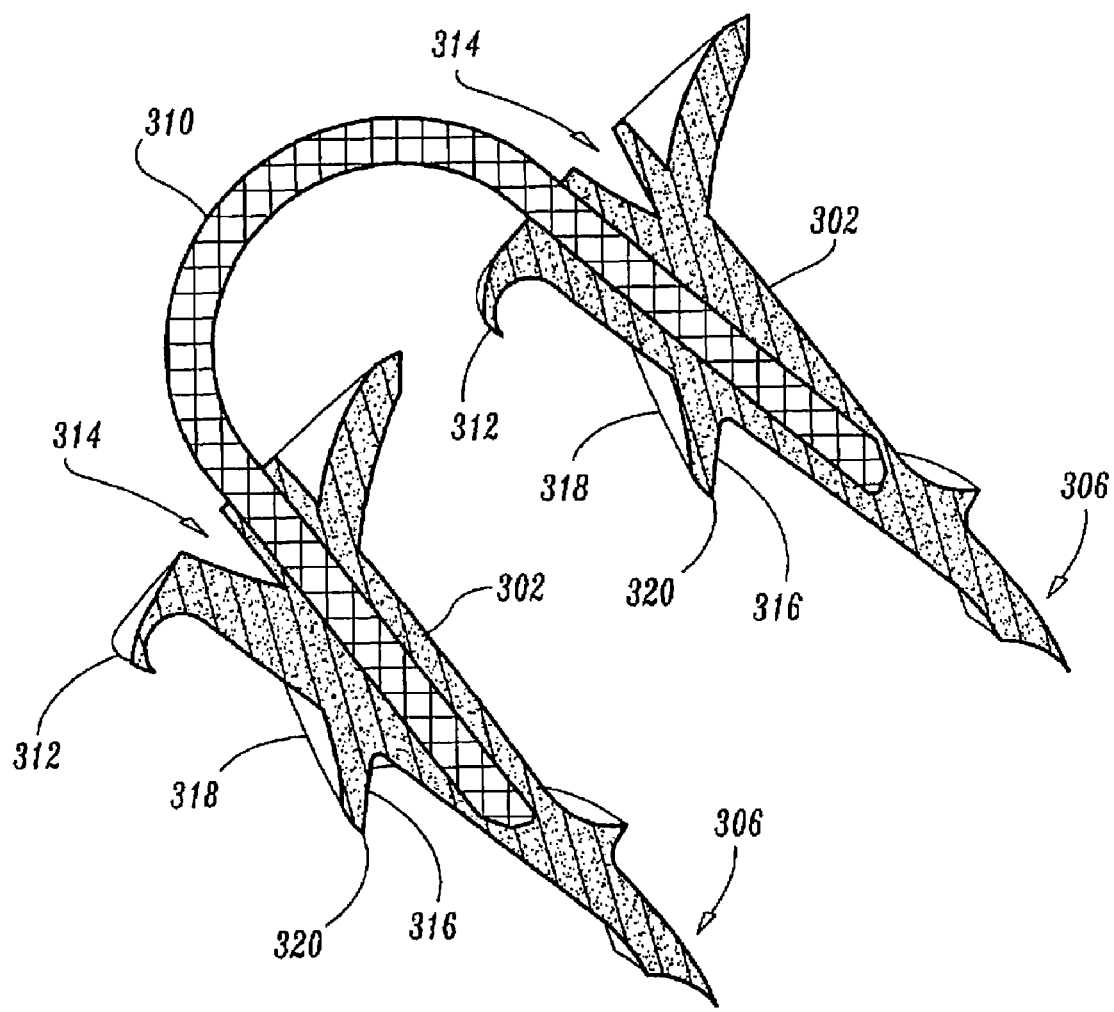
FIG. 6 is a cross-sectional view of the absorbable fastener shown in FIG. 5, taken along the longitudinal axis.

As seen in FIG. 6, helical thread 304 is made up of a distal surface 316 and a proximal surface 318 joined together to form a sharp edge 320. In addition, suture tether 310 is fixedly retained within anchors 302, however, it is envisioned that suture tether 310 can be rotatably mounted to proximal surface 308.

Fasteners 200 and 300 are also preferably made of medical grade absorbable materials, for example, Polyglycolic Acid (PGA) and Polylactic Acid (PLA). A critical feature of the presently disclosed absorbable fastener is that the absorbable fastener provide sufficient strength to retain a mesh material in place for a desired period of time. For example, in the case of applying a hernia repair mesh material, it is recommended that absorbable fasteners 200 or 300 remain in place retaining the mesh material for approximately 2-3 weeks and be absorbed into the body tissue anytime after that. In addition, it is preferred that absorbable fastener 200 and that each anchor of fastener apparatus 300 are approximately 3 mm long, from the tip of distal end to the proximal end, and wherein the proximal end is approximately 1.5 mm in diameter. It is preferred that fastener 200 and fastener apparatus 300 are configured and dimensioned to avoid penetrating too far into the body tissue.

Fasteners 200 and 300 can be imbedded into body tissue by either pressing the fastener in to the tissue and allowing the thread on the fastener to automatically twist the fastener into the tissue, by providing a twisting applier which turns the fastener and thus the helical threads draw the fastener into the body tissue or by a combination of pressing and twisting.

Figure 7:
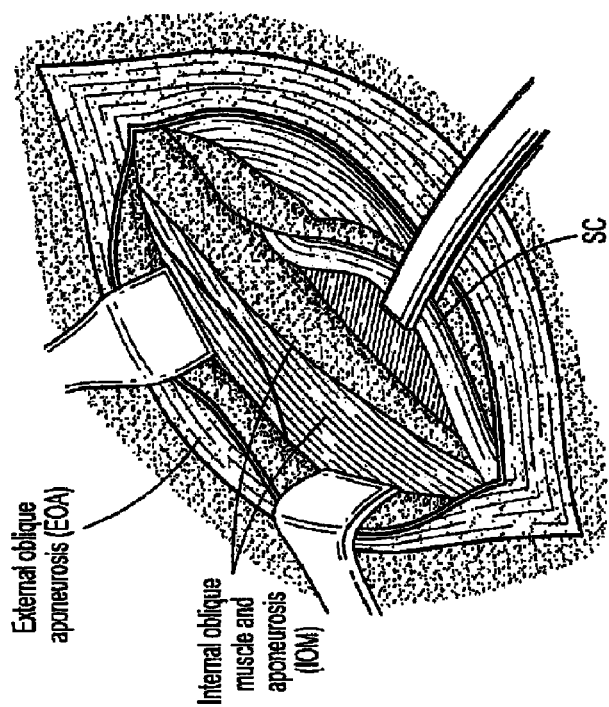
FIG. 7 is an illustration of a sequential step in one embodiment of attaching an object to body tissue using the presently disclosed absorbable surgical fasteners.

By way of example only, and not to be considered limiting in any way, with reference to FIGS. 7-11, a Lichtenstein repair method will now be described as performed using any of the absorbable surgical fasteners in accordance with the present disclosure. First, a 5 cm to 6 cm transverse incision is made within a Langer's line, beginning from the pubic tubercle. The external oblique aponeurosis ("EOA") is opened. As shown in FIG. 7, the spermatic cord ("SC") with its cremasteric covering, external spermatic vessels, and the genital nerve are freed from the inguinal floor and lifted with a Penrose drain. The spermatic cord ("SC") is dissected free from the pubic bone area for approximately 2 cm medial to the pubic tubercle in order to make room for extending a prosthetic mesh beyond the pubic tubercle. The external oblique aponeurosis ("EOA") is dissected from the underlying internal oblique muscle and aponeurosis ("IOM") high enough to make room for a prosthesis that is 6 cm to 7 cm in height. The sac is then dissected from the spermatic cord ("SC") beyond its neck and inverted into the properitoneal space without ligation or excision.

Figure 8:
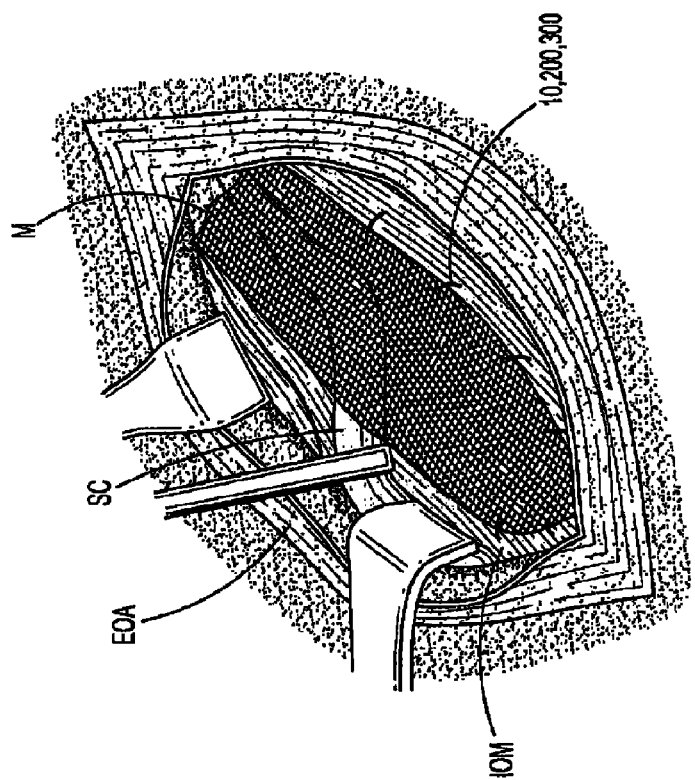
FIG. 8 is a further sequential step according to the method embodiment of FIG. 7.

Referring to FIG. 8, a medial side of a mesh ("M"), is shaped to the patient's anatomy. A first absorbable fastener 10, 200 or 300 is applied to the mesh to fix the mesh to the anterior rectus sheath where it inserts into the pubic bone. The absorbable fastener 10, 200 or 300 is placed approximately 2 cm medial to the pubic tubercle in order to be sure that the area is covered by the mesh ("M"). Additional absorbable fasteners 10, 200 or 300 are placed therearound and end at the lateral border of the internal ring. The lower edge of the mesh ("M") is then anchored to the inguinal ligament using the same fasteners 10, 200 or 300 around the surgical mesh ("M") and ending at the lateral border of the internal ring.

According to one method of the present disclosure, the absorbable fastener 10, 200 or 300 is secured into place by firing the fastener into the body tissue such that a first anchor of the surgical fastener penetrates through the surgical mesh and into the body tissue and such that a second anchor of the surgical fastener is implanted directly into the body tissue. In this manner, the suture tether 16, 310 (see FIGS. 1, 2, 5 and 6) of the fastener apparatus extends partially across the surgical mesh and partially across body tissue. In an alternative method, an absorbable fastener in accordance with the present disclosure, can be secured into place such that both anchors are imbedded into the body tissue and pass through the surgical mesh. If fasteners 200 are used in the method, fasteners 200 are anchored into the body tissue solely through the mesh.

Figures 9, 10:
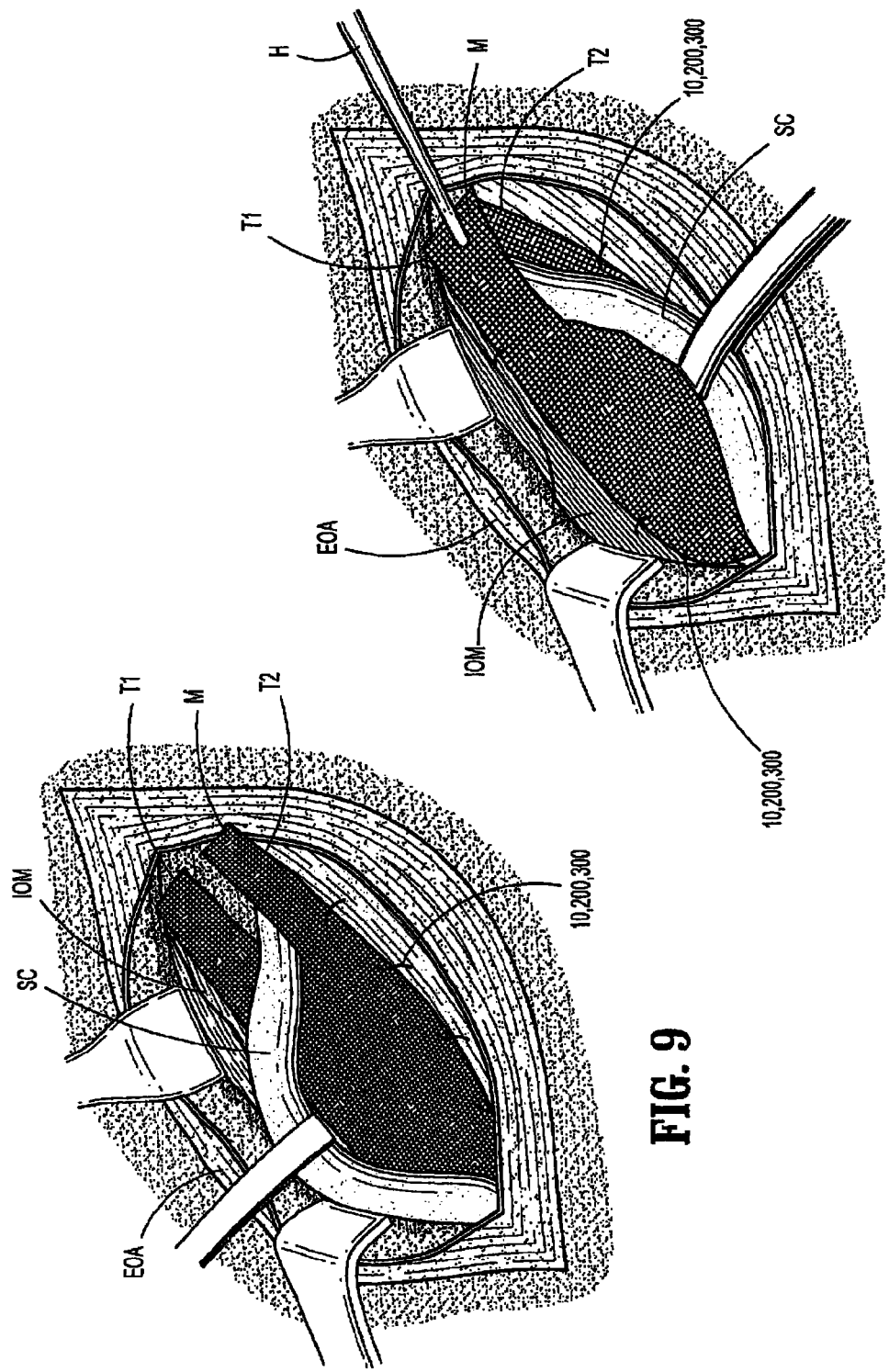
FIG. 9 is a still further sequential step of the method of FIG. 7.
FIG. 10 is another sequential step of the method of FIG. 7.

A slit is then made on the lateral end of the mesh ("M"), as seen in FIG. 9, creating 2 tails—⅔ above ("T1") and ⅓ below ("T2"). The upper tail ("T1") is then passed under the cord ("SC") and pulled toward the head of the patient, placing the spermatic cord ("SC") in between the 2 tails ("T1, T2"). The upper tail ("T1") is then crossed over the lower one ("T2") and held with a pair of hemostat ("H"), as seen in FIG. 10. The tails ("T1, T2") are later sutured together and tucked under the external oblique aponeurosis, leaving 5 cm to 6 cm of mesh lateral to the internal ring.

Figure 11:
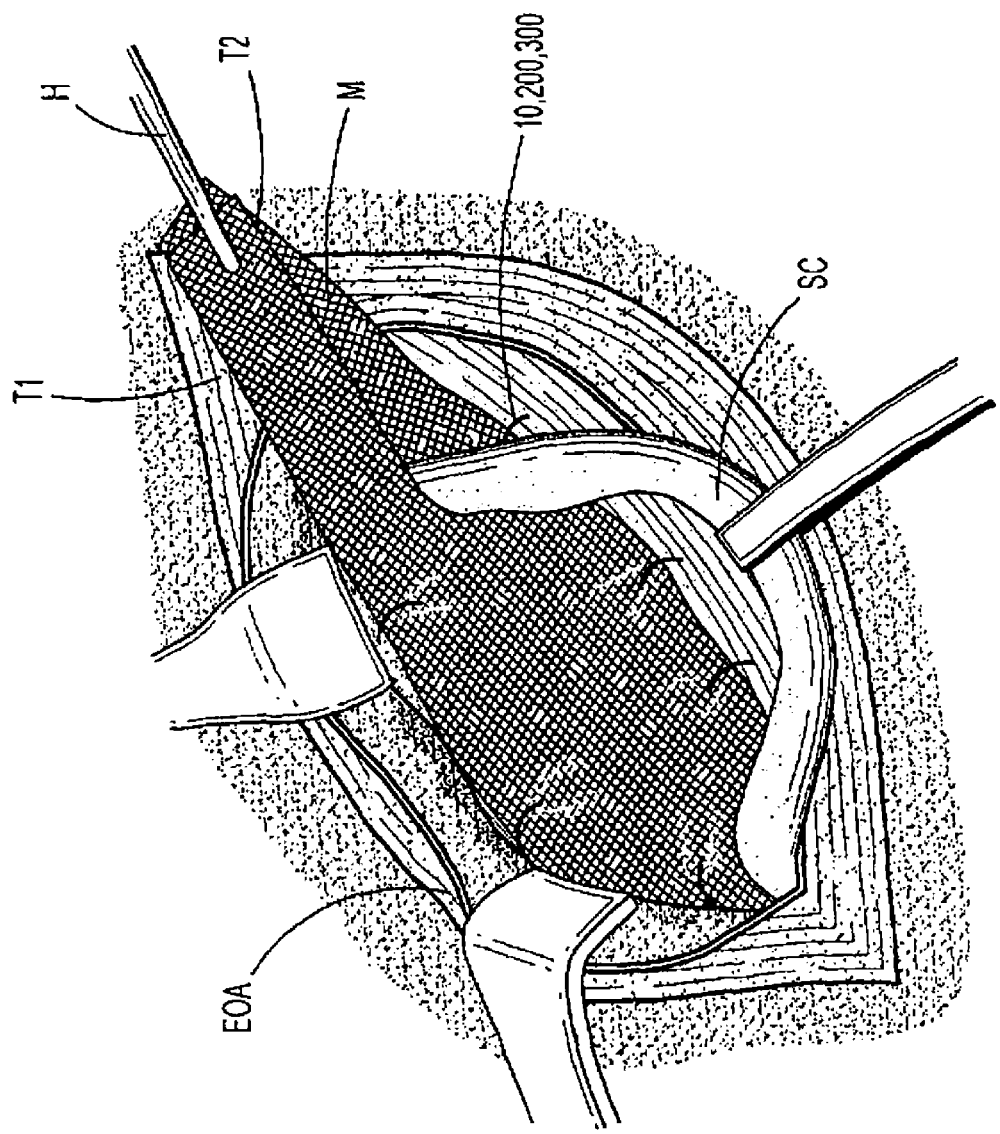
FIG. 11 is another illustration of a step of the method embodiment of FIG. 7.

While the upper edge of the mesh is fixed in place, care is taken to keep the mesh slightly relaxed. This laxity produces a dome-like ripple in the mesh to compensate for increased intra-abdominal pressure when the patient stands up from his or her recumbent position during the operation. If the mesh is kept completely flat, it becomes subject to tension when the patient stands up. This pulling effect on the mesh ("M") and the tissue, is illustrated when the mesh ("M") is kept flat as shown in FIG. 11. The use of a surgical fastener in accordance with the present disclosure effectively eliminates the tension of the surgical mesh since the anchors of the surgical fastener are relatively movable with respect to one another. In other words, one anchor is able to move with respect to the other anchor if needed as the patients body tissue shifts. In so doing, the tension on the mesh is reduced since the suture tether provides the mesh with some room to move since the individual anchors are moveable with respect to one another.

A Total ExtraPeritoneal Laparoscopic Hernia repair using fasteners 10 or 300, in accordance with the present disclosure, will now be described. First, a skin incision is created and the fascia is incised. A balloon type distractor is then placed therein and distended in order to create an operative extraperitoneal space. Umbilical trocars and secondary trocars are then inserted into the extraperitoneal space and the space explored. The medial and lateral structures are then dissected and the spermatic chord identified. A surgical mesh is then cut to the desired size and shape such that a slit is provided in order to wrap the mesh on either side of the spermatic chord. The mesh is then laterally fixed in place using surgical fasteners 10, 200 or 300 in order to anchor the mesh to the tranversus arch and the iliopubic tract. This step is repeated for the opposite side. The mesh is then medially fixed in place using additional fasteners 10, 200 or 300 to the transverses arch and to Cooper's ligament or in the alternative, fix the mesh to the medial iliopubic tract. Finally, the incision is closed.

It is envisioned that fasteners 10, 200 or 300 can be used in a TAPP repair method to replace suturing of the mesh both laterally and medially. In the TAPP repair method, fasteners 10, 200 or 300 are used to secure the mesh in to place by penetrating the mesh and being anchored into the body tissue.

While each of the above described fasteners have been described as being used in connection with hernial repair surgery, it is envisioned that fasteners having a similar structure can be used in surgical procedures for fastening items to bone or cartilage. In such surgical procedures, the surgical fasteners can be made from surgical grade stainless steel, titanium or any other surgical grade material having sufficient strength to penetrate bone.

It will be understood that various modifications may be made to the embodiments of the presently disclosed surgical absorbable fastener apparatus and methods disclosed herein. Therefore, the above description should not be construed as limiting, but merely as exemplifications of preferred embodiments. Those skilled in the art will envision other modifications within the scope and spirit of the present disclosure.

We claim:

1. A surgical fastener apparatus for securing a surgical mesh material to body tissue, comprising:
   a pair of substantially cylindrical bioabsorbable anchors each defining a longitudinal central axis, wherein each anchor is provided with a conically tapered distal end and a substantially planar proximal end, and wherein each anchor is further provided with a series of semicircular angled projections having a proximal surface that is angled with respect to the longitudinal axis in such a manner so as to define a partial thread, a tapered distal end, and defining a common central axis therethrough, wherein the common central axis of said series of angled projections, for each anchor, is spaced a radial distance from the longitudinal central axis of said respective anchor, wherein the pair of anchors are oriented with respect to one another such that the common central axis of the series of angled projections are disposed outward of the longitudinal central axes, and wherein an axial force is exerted along the common central axis of each of the series of angled projections; and
   a flexible tether interconnecting said proximal ends of said pair of anchors to enable freedom of movement of the anchors in multiple directions relative to one another, wherein said planar proximal surfaces of the angled projections are substantially orthogonal to the longitudinal central axis of each anchor.

2. The surgical fastener apparatus according to claim 1, wherein said pair of anchors are made from a bioabsorbable material.

3. The surgical fastener apparatus according to claim 2, wherein said bioabsorbable material is selected from a material which reabsorbs into said body tissue at an appropriate rate.

4. The surgical fastener apparatus according to claim 2, where said bioabsorbable material is selected from the group consisting of polyglycolic acid and polylactic acid.

5. The surgical fastener apparatus according to claim 1, where said pair of anchors and said tether are dimensioned to be partially absorbed into said body tissue for at least a period of approximately 2 to 3 weeks immediately after implanting and are fully absorbed into said body tissue at any time thereafter.

6. The surgical fastener apparatus according to claim 1, wherein said pair of anchors have a length of approximately 3 mm from a distal tip of said tapered distal end to said planar proximal end.

7. The surgical fastener apparatus according to claim 6, wherein said pair of anchors have a diameter of approximately 1.5 mm.

8. The surgical fastener apparatus according to claim 1, wherein said tether is made from a bioabsorbable material.

9. The surgical fastener apparatus according to claim 8, wherein said bioabsorbable material is selected from the group consisting of polyglycolic acid and polylactic acid.

10. The surgical fastener apparatus according to claim 1, wherein said tether is nonrigid.

11. A surgical fastener apparatus, for securing a surgical mesh material to body tissue, comprising:
    a pair of substantially cylindrical bioabsorbable anchors each defining a central longitudinal axis, wherein each anchor is provided with a conically tapered distal end and a substantially planar proximal end, and each anchor having angled projections formed on an outer surface thereof, wherein the angled projections for each anchor define a common longitudinal axis which is spaced a radial distance from the central longitudinal axis of the respective anchor, and wherein the angled projections are angled with respect to the longitudinal axis in such a manner so as to define a partial thread, wherein the pair of anchors are oriented with respect to one another such that the common longitudinal axes of the respective angled projections are disposed outward of the central longitudinal axes, and wherein an axial force is exerted along the common longitudinal axis of the respective angled projections of each anchor; and a flexible suture tether interconnecting said pair of anchors to one another to enable freedom of movement of the anchors in multiple directions relative to one another, wherein said angled projections include a series of semicircular angled projections each having a substantially planar proximal surface and a tapered distal end, and wherein said substantially planar proximal surfaces are substantially orthogonal to the central longitudinal axis of each anchor.

12. The surgical fastener apparatus according to claim 11, wherein said suture tether is operatively coupled to said planar proximal surface of each of said pair of anchors.

13. The surgical fastener apparatus according to claim 11, wherein said pair of anchors are made from a bioabsorbable material.

14. The surgical fastener apparatus according to claim 13, wherein said bioabsorbable material is selected from a material which reabsorbs into said body tissue at an appropriate rate.

15. The surgical fastener apparatus according to claim 13, where said bioabsorbable material is selected from the group consisting of polyglycolic acid and polylactic acid.

16. The surgical fastener apparatus according to claim 11, where said pair of anchors and said tether are dimensioned to be partially absorbed into said body tissue for at least a period of approximately 2 to 3 weeks immediately after implanting and are fully absorbed into said body tissue at any time thereafter.

17. The surgical fastener apparatus according to claim 11, wherein said pair of anchors have a length of approximately 3 mm from a distal tip of said tapered distal end to said planar proximal end.

18. The surgical fastener apparatus according to claim 17, wherein said pair of anchors have a diameter of approximately 1.5 mm.

19. The surgical fastener apparatus according to claim 11, wherein said tether is made from a bioabsorbable material.

20. The surgical fastener apparatus according to claim 19, wherein said bioabsorbable material is selected from the group consisting of polyglycolic acid and polylactic acid.

21. The surgical fastener apparatus according to claim 11, wherein said suture tether is fixedly secured to said pair of anchors.

* * * * *